United States Patent
Lim et al.

(10) Patent No.: US 7,671,993 B2
(45) Date of Patent: Mar. 2, 2010

(54) METHODS AND APPARATUS FOR ESTIMATING THE INTENSITY OF ONE SPECTRUM OF LIGHT IN A MIXED LIGHT, IN RESPONSE TO THE SENSED INTENSITIES OF ONE OR MORE OTHER SPECTRUMS OF LIGHT IN THE MIXED LIGHT

(75) Inventors: Len-Li Kevin Lim, Perak (MY); Ken A. Nishimura, Fremont, CA (US)

(73) Assignee: Avago Technologies ECBU IP (Singapore) Pte. Ltd., Singapore (SG)

( * ) Notice: Subject to any disclaimer, the term of this patent is extended or adjusted under 35 U.S.C. 154(b) by 381 days.

(21) Appl. No.: 11/698,715

(22) Filed: Jan. 25, 2007

(65) Prior Publication Data

US 2008/0180671 A1  Jul. 31, 2008

(51) Int. Cl.
*G01J 3/51* (2006.01)

(52) U.S. Cl. .................. 356/419; 356/425; 250/205

(58) Field of Classification Search .................. 356/419, 356/425; 250/205
See application file for complete search history.

(56) References Cited

U.S. PATENT DOCUMENTS

| 5,917,621 A | 6/1999 | Yushiya | |
|---|---|---|---|
| 6,163,377 A * | 12/2000 | Boles et al. | 356/419 |

FOREIGN PATENT DOCUMENTS

| CN | 88102056 | 9/1988 |
|---|---|---|
| DE | 4438905 | 11/1995 |

* cited by examiner

*Primary Examiner*—F. L Evans

(57) ABSTRACT

In one embodiment, light having a first spectrum is filtered from a mixed light. Light having a second spectrum, different from the first spectrum, is also filtered from the mixed light. An intensity of the light having the first spectrum, and an intensity of the light having the second spectrum, are then sensed. From the sensed intensities of the lights having the first and second spectrums, an intensity of light having a third spectrum is estimated.

25 Claims, 5 Drawing Sheets

US 7,671,993 B2

METHODS AND APPARATUS FOR ESTIMATING THE INTENSITY OF ONE SPECTRUM OF LIGHT IN A MIXED LIGHT, IN RESPONSE TO THE SENSED INTENSITIES OF ONE OR MORE OTHER SPECTRUMS OF LIGHT IN THE MIXED LIGHT

BACKGROUND

Lighting systems such as liquid crystal display (LCD) backlights sometimes comprise red, green and blue (RGB) light-emitting diodes (LEDs). Together, the RGB LEDs can be used to produce a mixed light (e.g., a white light in the case of an LCD backlight).

System manufacturing variations, operating conditions, LED aging, and other factors can cause the intensity and color of individual ones of a lighting system's LEDs to drift. As a result, an optical feedback system employing one or more photosensors is often used to measure the intensity and/or color point of the mixed light produced by an LED lighting system. The feedback system's outputs are then used to regulate the drive signals, and thus the intensities, of individual ones or groups of the lighting system's LEDs.

BRIEF DESCRIPTION OF THE DRAWINGS

Illustrative embodiments of the invention are illustrated in the drawings, in which.

DETAILED DESCRIPTION

As previously indicated, lighting systems such as LCD backlights sometimes comprise RGB LEDs. Together, the RGB LEDs can be used to produce a mixed light (e.g., a white light in the case of an LCD backlight).

System manufacturing variations, operating conditions, LED aging, and other factors can cause the intensity and color of individual ones of a lighting system's LEDs to drift. As a result, an optical feedback system employing one or more photosensors is often used to measure the intensity and/or color point of the mixed light produced by an LED lighting system. The feedback system's outputs are then used to regulate the drive signals, and thus the intensities, of individual ones or groups of the lighting system's LEDs.

A problem with conventional optical feedback systems is that they poorly measure the intensity of the "visible red" wavelengths in a mixed light. This is because the pigments that are used to filter out the red wavelengths of a mixed light do not cut off the longer and "non-visible red" wavelengths, such as infrared (IR) wavelengths.

Figure 1:
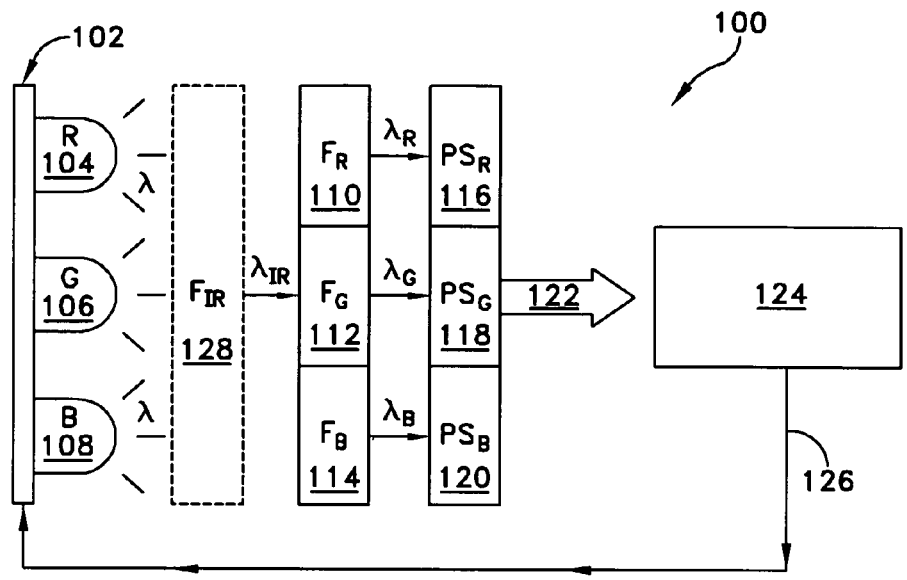
FIG. 1 illustrates a first exemplary system for measuring the intensities of red, green and blue wavelengths of a mixed light.

FIG. 1 illustrates an exemplary system 100 comprising a light source 102 for producing a mixed light ($\lambda$). Assuming, for a moment, that the IR filter 112 (FIR) is not present, the mixed light ($\lambda$) falls incident on a plurality of filters 110, 112, 114 (FR, FG, FB) that respectively pass only red, green and blue wavelengths ($\lambda_R$, $\lambda_G$, $\lambda_B$) of the mixed light. The filtered red, green and blue wavelengths ($\lambda_R$, $\lambda_G$, $\lambda_B$) of the mixed light then fall incident on respective red, green and blue photosensors 116, 118, 120 ($PS_R$, $PS_G$, $PS_B$) that are positioned to respectively sense the intensities of the red, green and blue wavelengths. Signals 122 produced by the photosensors 116, 118, 120 are used by a control system 124 to determine whether the intensities of the red, green and blue wavelengths need to be adjusted to produce a mixed light of a desired intensity and/or color point. Appropriate drive signals 126 are then provided for regulating the light output of various elements of the light source 102. For example, if the light source 102 comprises red (R), green (G) and blue (B) LEDs 104, 106, 108, the control system 124 may provide different drive signals for different-colored ones of the RGB LEDs.

Figure 2:
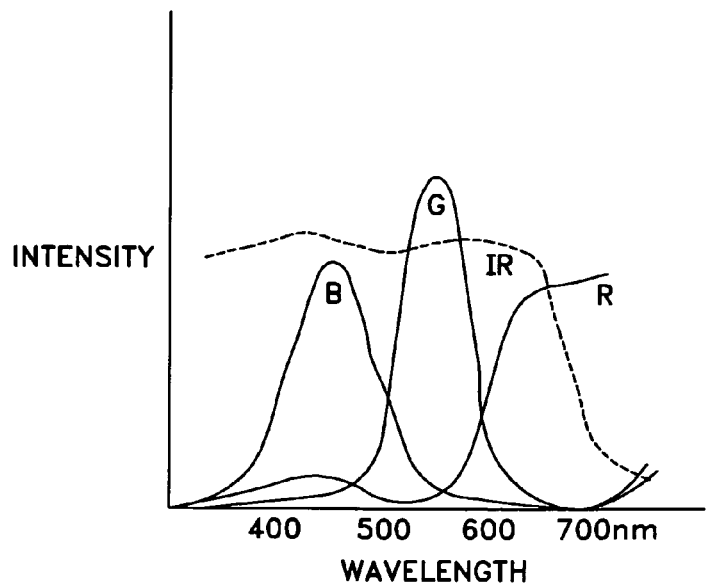
FIG. 2 illustrates a graph of exemplary red, green and blue light intensities that may be sensed by the FIG. 1 system.

FIG. 2 illustrates a graph of exemplary RGB light intensities that may be sensed by the system 100 (FIG. 1). Of note, each of the photosensors 116, 118, 120 produces a signal that is indicative of the aggregate intensity of the light falling within a particular range of light wavelengths. Thus, for example, the red, green and blue photosensors 116, 118, 120 shown in FIG. 1 may produce respective signals corresponding to the aggregate intensities of light within the R, G and B "humps" of the graph shown in FIG. 2. Note, however, that when using a typical pigment-based red filter 110, there is no upper limit to the wavelengths of light passed by the red filter 110. Thus, the R "hump" in the FIG. 2 graph is not closed. This unclosed hump is indicative of the fact that red filters typically allow the passage of red wavelengths that exceed the visible light band. This is problematic, in that optical feedback systems typically need to sense and adjust the "visible" light that is generated by a lighting system.

One solution to the afore-mentioned problem is to filter IR wavelengths from the mixed light. The system 100 (FIG. 1) therefore shows an IR filter 128 ($F_{IR}$) that may be used for this purpose. The IR filter 128, in combination with the red filter 110, serves to close the R "hump" shown in FIG. 2.

As shown in FIG. 2, the nature of an IR filter 128 can lead to a clipping of the intensities of other wavelengths (such as green wavelengths). More significantly, however, an IR filter 128 is often formed of glass, and this adds both cost and height to an optical feedback system.

Figure 3:
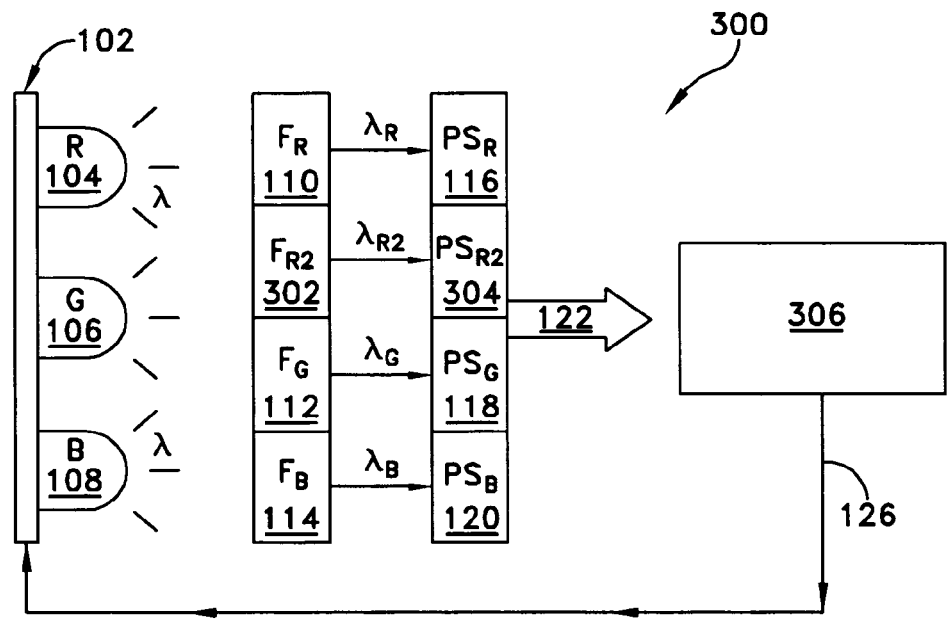
FIG. 3 illustrates exemplary apparatus for measuring the intensities of different ranges of red light wavelengths in a mixed light and, in response thereto, estimating the intensity of the visible red wavelengths of the mixed light.

FIG. 3 shows a first exemplary alternative to the system 100. In the system 300, the IR filter 128 is eliminated, and a second red filter 302 ($F_{R2}$) and corresponding photosensor 304 ($PS_{R2}$) are included instead. The second red filter 302 receives the mixed light ($\lambda$) and passes only red wavelengths ($\lambda_{R2}$) of the mixed light. However, the transmission characteristic of the second red filter 302 differs from that of the first red filter 110, such that the range of red wavelengths ($\lambda_{R2}$) passed by the second red filter 302 differs from the range of red wavelengths ($\lambda_R$) passed by the first red filter 110. Of note, both of the red filters 110, 302 are open-ended filters (i.e., each filter only filters out or removes light wavelengths at one end of its range).

The photosensor 304 is positioned to sense the intensity of the red wavelengths passed by the second red filter 302. A color estimation and/or control system 306 then receives signals 122 from the green and blue photosensors 118, 120, and generates drive signals 126 to regulate the green and blue elements 106, 108 of the light source 102 in a conventional way. However, the color estimation and/or control system 306 generates a drive signal 126 for regulating the red element 104 of the light source 102 by 1) receiving signals 122 corresponding to the intensities of the first and second red light wavelengths ($\lambda_R$, $\lambda_{R2}$) sensed by the first and second red photosensors 116, 304, and then 2) synthesizing an output of a bandpass filter for visible red light by receiving, and applying an algorithm to, the intensities of the first and second red light wavelengths ($\lambda_R$, $\lambda_{R2}$).

Figure 4:
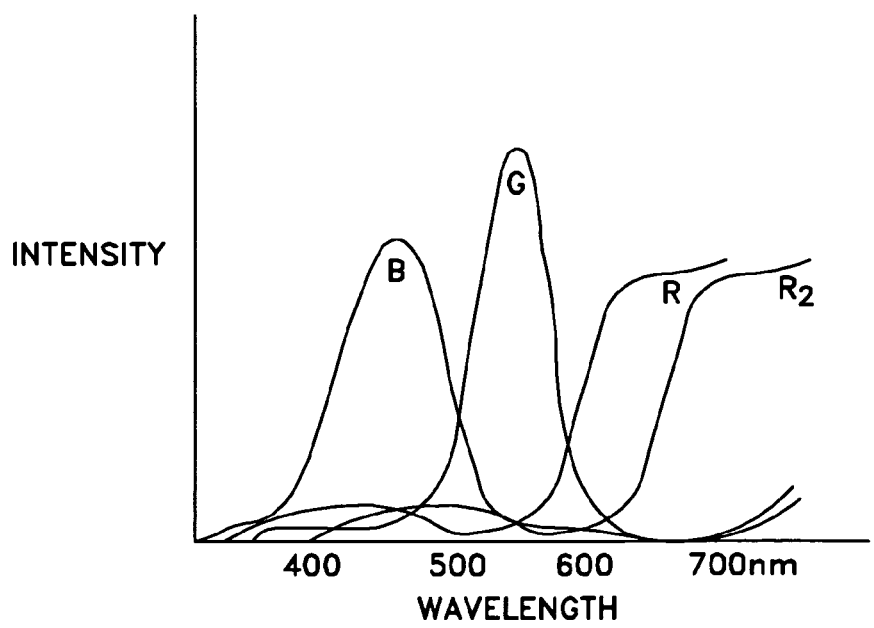
FIG. 4 illustrates a graph of exemplary first red, second red, green and blue light intensities that may be sensed by the FIG. 3 system.

As shown in FIG. 4, the transmission characteristic of the first red filter 110 removes light having a wavelength shorter than a first value, and the transmission characteristic of the second red filter 302 removes light having a wavelength shorter than a second value. If the filters 110, 302 are chosen such that the first and second values bound a range of wavelengths that substantially define a visible red light spectrum, then the color estimation and/or control system 306 may estimate the intensity of the visible red light wavelengths by subtracting the intensity of the second red light wavelengths ($\lambda_{R2}$) from the intensity of the first red light wavelengths ($\lambda_R$). In one embodiment of the system 300, the "first value" defines a lower cutoff for the transmission characteristic of the first red filter 110, at a light wavelength between 620 and 650 nanometers (and preferably, at about 630 nanometers). Similarly, the "second value" may define a lower cutoff for the transmission characteristic of the second red filter 302, at a light wavelength between 650 and 680 nanometers (and preferably, at about 670 nanometers).

In some embodiments of the system 300 (FIG. 3), the first and second red filters 110, 302 may be chosen such that the lower cutoffs of their transmission characteristics do not bound the visible red light spectrum, but instead bound only a portion of the visible red light spectrum. Or, the lower cutoffs of the two filters 110, 302 may bound some or all of the visible red light spectrum, as well as other light wavelengths such as orange or yellow wavelengths. In these embodiments, the system 300 may not be able to estimate the intensity of the visible red light spectrum as accurately as a system where the lower cutoffs of the filters 110, 302 bound only the visible red light spectrum. However, the systems described in this paragraph may be accurate enough to regulate red light sources in some applications.

Figure 5:
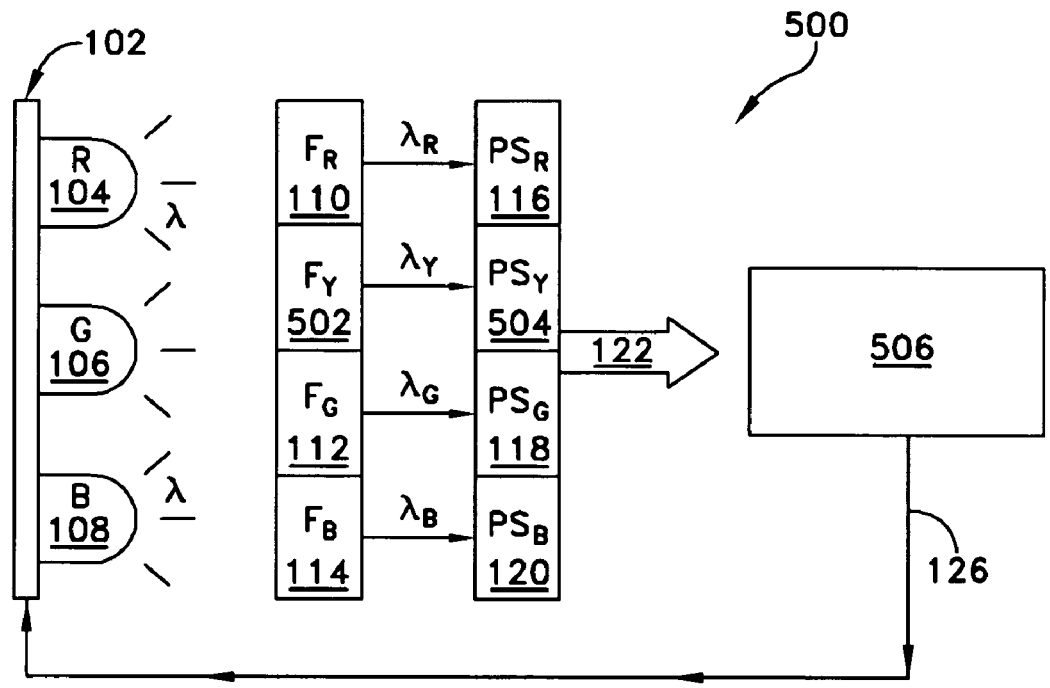
FIG. 5 illustrates exemplary apparatus for measuring the intensities of red and yellow light wavelengths in a mixed light and, in response thereto, estimating the intensity of the visible red wavelengths of the mixed light.

FIG. 5 shows a second exemplary alternative to the system 100. In the system 500, the IR filter 128 is eliminated, and a yellow or orange filter 502 ($F_Y$) and corresponding photosensor 504 ($PS_Y$) are included instead. The yellow (or orange) filter 502 receives the mixed light ($\lambda$) and passes a range of light wavelengths that includes a range of yellow and/or orange light wavelengths ($\lambda_Y$), in addition to a range of red light wavelengths of the mixed light. The photosensor 504 ($PS_Y$) is positioned to sense the intensity of the light wavelengths passed by the filter 502. A color estimation and/or control system 506 then receives signals 122 from the green and blue photosensors 118, 120, and generates drive signals 126 to regulate the green and blue elements 106, 108 of the light source 102 in a conventional way. However, the color estimation and/or control system 506 generates a drive signal 126 for regulating the red element 104 of the light source 102 by 1) receiving signals 122 corresponding to the intensities of the red and yellow light wavelengths ($\lambda_R$, $\lambda_Y$) sensed by the red and yellow photosensors 116, 504, and then 2) estimating the intensity of the visible red wavelengths of the mixed light ($\lambda$) in response to the intensities of both the red and yellow light wavelengths (and, in some cases, in response to the intensity of the green light wavlengths ($\lambda_G$) sensed by the green photosensor 118).

Figure 6:
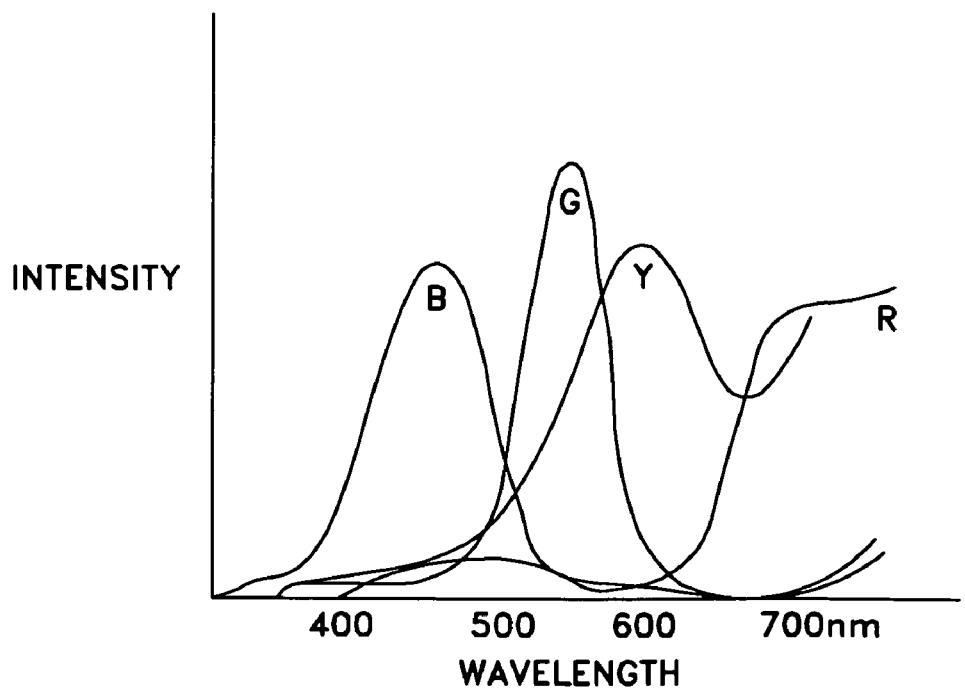
FIG. 6 illustrates a first exemplary graph of red, green, blue and yellow light intensities that may be sensed by the FIG. 5 system.
Figure 7:
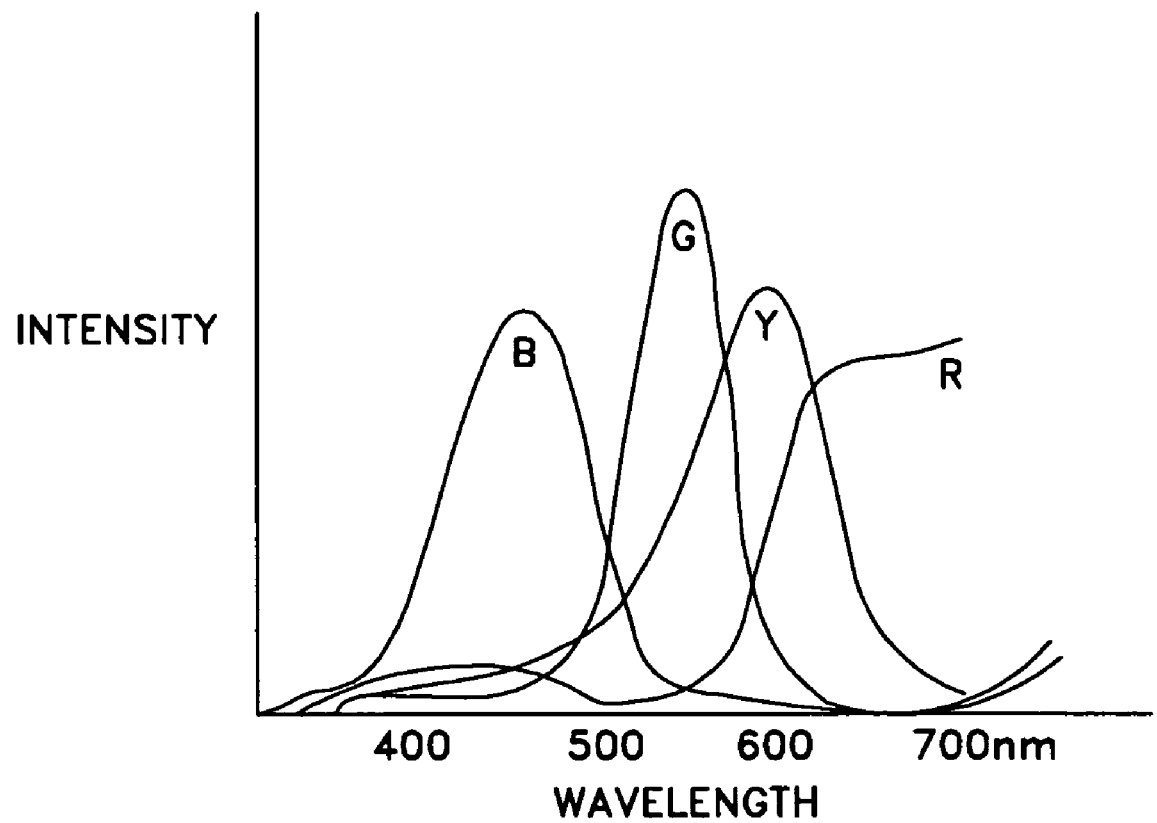
FIG. 7 illustrates a second exemplary graph of red, green, blue and yellow light intensities that may be sensed by the FIG. 5 system.

FIG. 6 illustrates a first set of exemplary responses for the filters 116, 118, 120, 504 shown in FIG. 5. In FIG. 6, it is assumed that the filters 116, 118, 120, 504 are pigment-based filters. FIG. 7 illustrates a second set of exemplary responses for the filters 116, 118, 120, 504. In FIG. 7, it is assumed that one or more of the filters 116, 118, 120, 504 are interference-type filters. The exemplary filter responses shown in FIGS. 6 & 7 are discussed below in more detail.

As shown in FIG. 6, the transmission characteristic of a pigment-based yellow filter 502 will typically only remove light having a wavelength shorter than a first value. If this first value is a yellow light wavelength, then the yellow filter 502 may pass both yellow light wavelengths, as well as visible and non-visible red light wavelengths. Similarly to the yellow filter 502, the transmission characteristic of a pigment-based red filter 110 may remove light having a wavelength shorter than a second value. If this second value is a wavelength at or about the boundary between visible and non-visible red light wavelengths, then the red filter 110 may pass non-visible red light wavelengths. In contrast to the yellow and red filters 502, 110, the transmission characteristics (G, B) of pigment-based green and blue filters 112, 114 may be substantially closed about ranges of green or blue light wavelengths. However, pigment-based green and blue filters 112, 114 may begin to "open up" at about 700 nanometers (i.e., they may allow light wavelengths of 700 nanometers or greater to pass).

If the first and second values that define the lower light cutoffs for the yellow and red filters 502, 110 are chosen such that they bound a range of wavelengths that includes i) at least a portion of the light wavelengths falling within the visible red light spectrum, and ii) a range of wavelengths that overlaps at least some of the wavelengths passed by the green filter 112 (e.g., yellow wavelengths), then the color estimation and/or control system 506 may estimate the intensity of the visible red light spectrum by applying an algorithm to the light intensities passed by the yellow filter 502, red filter 110 and green filter 112. For example, both 1) the intensity of the light wavelengths passed by the red filter 110, and 2) a portion of the intensity of the light wavelengths passed by the green filter 112, may be subtracted from 3) the intensity of the light wavelengths passed by the yellow filter 502. In this manner, the intensity of the green light wavelengths passed by the green filter 112 can be used to at least partially compensate for a filter 502 that passes wavelengths shorter than those falling within a visible red light spectrum. Alternately, and if the green filter 112 "opens up" sufficiently above 700 nanometers, it may not be necessary to subtract the intensity of the red light wavelengths from the intensity of the yellow light wavelengths. This is because subtracting the intensity of the light wavelengths passed by the green filter 112, which includes the intensity of red wavelengths above 700 nanometers, may adequately remove the intensity of non-visible red light wavelengths from the intensity of the light wavelengths passed by the yellow filter 502.

As shown in FIG. 7, the transmission characteristic of an interference-type yellow filter may allow for passage of a closed band of wavelengths (as opposed to a single yellow wavelength). This band of wavelengths (Y) may lie primarily between red and green bands of wavelengths, and may in one case include wavelengths ranging from about 565-590 nanometers. However, the band of wavelengths (Y) may also have a significant overlap with other bands of wavelengths, including the red wavelengths (R). As a result, and through experimentation and/or modeling, a relationship between the sensed intensities of red wavelengths and yellow wavelengths may be developed, and this relationship may then be used to estimate the intensity of the "visible red" wavelengths of a mixed light (and ultimately regulate a red element (e.g., a red LED) of a light source). In one embodiment, the color estimation and/or control system 506 may use the intensities of light wavelengths passed by the yellow and red filters 110, 502 to index a table that identifies the intensity of a light spectrum that is substantially bounded by the upper wavelength cutoff of the "Y" band of wavelengths and the lower wavelength cutoff of the "R" band of wavelengths. In another embodiment, the color estimation and/or control system 506 may use the intensities of light wavelengths passed by the yellow and red filters 110, 502 to index a table that identifies the intensity of a light spectrum that is shifted more toward one or the other of the "Y" or "R" bands. As described with respect to FIG. 6, an intensity of green light wavelengths may be used to adjust any of the above estimated intensities.

Although the teachings in the above paragraph have special applicability to determining the intensity of visible red light wavelengths, they may be used to determine the intensity of any spectrum of light wavelengths. In this regard, light sensing apparatus may generally comprise a first light filter having a first transmission characteristic, and a second light filter having a second transmission characteristic, wherein the second transmission characteristic differs from the first transmission characteristic. One or more photosensors may then be positioned to sense i) an intensity of light wavelengths passed by the first light filter, and ii) an intensity of light wavelengths passed by the second light filter. Thereafter, a color estimation system may receive the light intensities passed by the first and second light filters, and in response thereto, i) synthesize an output of a bandpass filter by ii) receiving, and applying an algorithm to, the light intensities passed by the first and second filters. In some embodiments, the intensities of light sensed by other filters may be incorporated into the algorithm.

In addition to subtraction (or instead of), the algorithm mentioned in the above paragraph may incorporate other operations, such as addition, averaging, the multiplication of one or more light intensities by a percentage, or the use of one or more light intensities to lookup one or more data values. The manner in which the intensities received by the color estimation system are combined, differentiated or used depends on the particular estimation algorithm that one desires to implement.

In addition to the above-described apparatus for sensing light, the following method may be used to estimate the intensity of a light spectrum. First, light having a first spectrum and light having a second spectrum may be filtered from a mixed light. The intensity of the light having the first spectrum, and the intensity of the light having the second spectrum, are then sensed. Thereafter, the sensed intensities of the first and second spectrums may be used to estimate the intensity of light having a third spectrum.

Figure 8:
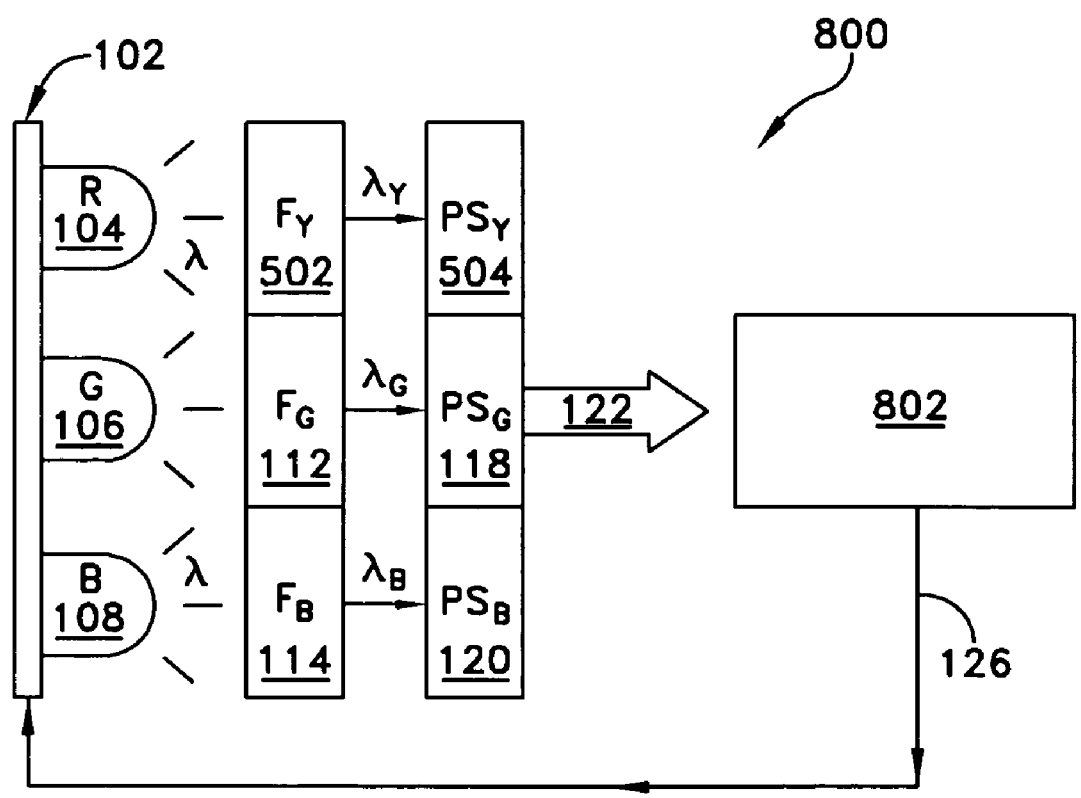
FIG. 8 illustrates exemplary apparatus for measuring the intensity of yellow light wavelengths in a mixed light and, in response thereto, estimating the intensity of the visible red wavelengths of the mixed light.

FIG. 8 shows a third exemplary alternative to the system 100. In the system 800, the IR filter 128 in the system 100 (FIG. 1) is eliminated, and a yellow (or orange) filter 502 ($F_Y$) and corresponding photosensor 504 ($PS_Y$) replace the red filter 110 and red photosensor 116. A color estimation and/or control system 802 then generates a drive signal 126 for regulating the red element 104 of the light source 102 by 1) receiving a signal 122 corresponding to the intensity of yellow or orange wavelengths of light sensed by the photosensor 504, and then 2) estimating the intensity of the visible red wavelengths of the mixed light ($\lambda$) in response to the intensity of the yellow wavelengths alone.

Through experimentation and/or modeling, a relationship between the intensities of red and yellow wavelengths may be developed, and this relationship may then be used by the system 802 to estimate the intensity of the "visible red" wavelengths of a mixed light (and ultimately regulate a red element (e.g., a red LED) of a light source).

In one embodiment, the color estimation and/or control system 802 may use the intensity of light wavelengths passed by the yellow filter 502 to index a table that identifies the estimated intensity of the visible red light spectrum.

Although the regulation of a red light source (or element of a mixed light source) based on the sensed intensity of yellow wavelengths, alone, may not provide the same degree of accuracy as the regulation of a red light source based on the sensed intensities of both red and yellow wavelengths of light, the degree of accuracy provided by a yellow-only system may often be 1) acceptable, 2) better than the degree of accuracy provided by a system that regulates a red light source based on the sensed intensity of only red wavelengths of light, and/or 3) cheaper than a system that regulates a red light source based on the sensed intensities of both red and yellow wavelengths of light.

Although the teachings in the above paragraph have special applicability to determining the intensity of visible red light wavelengths, they may be applied to determining the intensity of any spectrum of light wavelengths. In this regard, light sensing apparatus may comprise 1) a light filter having a transmission characteristic, 2) a photosensor that is positioned to sense the intensity of light wavelengths passed by the light filter, and 3) a color estimation system to receive the intensity of light wavelengths passed by the light filter, and in response thereto, estimate an intensity of light having a spectrum that overlaps, but is shifted with respect to, the transmission characteristic of the light filter.

In addition to the above-described apparatus for sensing light, the following method may be used to sense the intensity of a light spectrum. First, light having a first spectrum may be filtered from a mixed light. The intensity of the light having the first spectrum may then be sensed, and the intensity of a second spectrum of light may be estimated based on the intensity of the light having the first spectrum. The second spectrum overlaps, but is shifted from, the first spectrum.

The photosensors discussed herein may take various forms, including those of photodiodes or phototransistors. Preferably, all of a system's photosensors are formed in parallel (i.e., at the same time), on a single substrate, using a common fabrication process.

The filters discussed herein may also take various forms, but are preferably applied as coatings on a substrate in which one or more of the photosensors are formed. Alternately, the filters may be formed on one or more glass or plastic plates, or may be included within a color wheel. In the latter case, the color wheel may be moved with respect to a single photosensor, and the single photosensor may alternately sense the intensities of different-colored wavelengths of light.

The light sources discussed herein (which may sometimes take the form of components or elements of other light sources) may take the form of solid-state light sources, such as LEDs or laser diodes. Alternately, they may take the form of incandescent, fluorescent or other light sources.

By way of example, the color estimation and/or control systems 300, 500, 800 are shown as unitary structures. However, their functionality can alternately be distributed between two or more structures. For example, color estimation functions may be relegated to a first structure (e.g., a logic circuit or processor), and the generation of drive signals may be relegated to a second structure (e.g., a second logic circuit or processor).

In some cases, a color estimation system may not be used to regulate the drive signal(s) of a light source, but may instead be used for the purpose of reporting color information (e.g., different-colored light intensities, or a color point) to a system that monitors a light source's intensity or color point for other purposes (e.g., for indicating when a light source should be replaced, or for indicating how color input should be post-processed or corrected).

What is claimed is:

1. Apparatus, comprising:
   a first light filter having a first transmission characteristic;
   a second light filter having a second transmission characteristic, wherein the second transmission characteristic differs from the first transmission characteristic;
   at least one photosensor, positioned to sense i) an intensity of light wavelengths passed by the first light filter, and ii) an intensity of light wavelengths passed by the second light filter; and
   a color estimation system to i) synthesize an output of a bandpass filter by ii) receiving, and applying an algorithm to, the intensities of the light wavelengths passed by the first and second light filters.

2. The apparatus of claim 1, wherein:
   the first transmission characteristic removes light having a wavelength shorter than a first value; and
   the second transmission characteristic removes light having a wavelength shorter than a second value.

3. The apparatus of claim 2, wherein the first value is about 630 nanometers, and wherein the second value is about 670 nanometers.

4. The apparatus of claim 2, wherein the first value is between 620 and 650 nanometers, and wherein the second value is between 650 and 680 nanometers.

5. The apparatus of claim 2, wherein the first value and the second value substantially bound a visible red light spectrum.

6. The apparatus of claim 2, wherein the first value and the second value bound a range of light wavelengths that includes at least a portion of a visible red light spectrum.

7. The apparatus of claim 2, wherein the algorithm comprises subtraction.

8. The apparatus of claim 2, wherein the first and second transmission characteristics do not have long wavelength cutoffs.

9. The apparatus of claim 2, further comprising:
   a third light filter having a third transmission characteristic, wherein the third transmission characteristic is different from the first and second transmission characteristics;
   wherein one of the at least one photosensor is positioned to sense an intensity of light wavelengths passed by the third light filter; and
   wherein the color estimation synthesizes the output of the bandpass filter by further receiving, and applying an algorithm to, the intensity of the light wavelengths passed by the third light filter.

10. The apparatus of claim 9, wherein the third transmission characteristic removes light having a wavelength shorter than a third value and longer than a fourth value, and wherein a range of light wavelengths bounded by the third and fourth values includes at least some of the light wavelengths bounded by the first and second values.

11. The apparatus of claim 10, wherein the third light filter is a green light filter, and wherein the first value and the second value bound a range of light wavelengths that includes at least a portion of a visible red light spectrum.

12. The apparatus of claim 1, wherein the algorithm comprises subtraction.

13. The apparatus of claim 1, wherein the first and second transmission characteristics are substantially limited to different ranges of red light wavelengths.

14. The apparatus of claim 1, further comprising a control system to, in response to the synthesized output of the bandpass filter, generate a signal for regulating a red light source that, along with other light in a mixed light, illuminates the first and second light filters.

15. The apparatus of claim 14, further comprising:
   a green light filter;
   a blue light filter;
   a green photosensor, positioned to sense an intensity of light wavelengths passed by the green filter;
   a blue photosensor, positioned to sense an intensity of light wavelengths passed by the blue filter; and
   a control system to, in response to the intensities of light wavelengths that are respectively passed by the green and blue light filters, respectively generate signals for regulating a green light source and a blue light source that respectively illuminate at least the green and blue light filters.

16. The apparatus of claim 15, further comprising the red, green and blue light sources, wherein the red, green and blue light sources comprise red, green, and blue solid state light emitting elements.

17. The apparatus of claim 15, further comprising the red, green and blue light sources, wherein the red, green and blue light sources comprise at least red, green, and blue light emitting diodes.

18. The apparatus of claim 1, wherein the first light filter is a yellow light filter, and the second light filter is a red light filter.

19. The apparatus of claim 1, wherein the first light filter is an orange light filter, and the second light filter is a red light filter.

20. The apparatus of claim 1, wherein each of the at least one photosensor comprises a photodiode.

21. The apparatus of claim 1, wherein the at least one photosensor comprises:
   a first photosensor to sense the intensity of light wavelengths passed by the first light filter; and
   a second photosensor to sense the intensity of light wavelengths passed by the second light filter.

22. A method, comprising:
   filtering, from a mixed light, light having a first spectrum;
   filtering, from the mixed light, light having a second spectrum, wherein the second spectrum is different from the first spectrum;
   sensing an intensity of the light having the first spectrum, and an intensity of the light having the second spectrum; and
   estimating from the intensities of the lights having the first and second spectrums, an intensity of light having a third spectrum.

23. The method of claim 22, wherein the third spectrum is substantially limited to visible red wavelengths of the mixed light.

24. The method of claim 22, wherein estimating the intensity of the light having the third spectrum comprises subtracting the intensity of the light having the second spectrum from the intensity of the light having the first spectrum.

25. The method of claim 22, wherein estimating the intensity of the light having the third spectrum comprises using the intensity of the light having the first spectrum, and the intensity of the light having the second spectrum, to index a table identifying the intensity of the light having the third spectrum.

* * * * *